United States Patent [19]

Buhmann et al.

[11] Patent Number: 4,783,459
[45] Date of Patent: Nov. 8, 1988

[54] ANILINOPYRIMIDINE FUNGICIDES

[75] Inventors: Ulrich Buhmann; Jurgen Westermann; Dietrich Baumert; Ernst Pieroh, all of Berlin, Fed. Rep. of Germany; Geoffrey R. Cliff, Whittlesford; Ian C. Richards, Haverhill, both of England

[73] Assignee: Schering Agrochemicals Ltd., United Kingdom

[21] Appl. No.: 41,706

[22] Filed: Apr. 23, 1987

[30] Foreign Application Priority Data

Apr. 23, 1986 [DE] Fed. Rep. of Germany ....... 3614060

[51] Int. Cl.$^4$ ............. C07D 239/02; C07D 401/00; C07D 413/00; C07F 5/02
[52] U.S. Cl. ........................... 514/235.8; 544/330; 544/331; 544/332; 544/122; 544/229; 514/275
[58] Field of Search .............. 544/330, 331, 332, 122, 544/229; 514/275, 228, 230, 234, 236, 237, 233

[56] References Cited

U.S. PATENT DOCUMENTS 2,748,124 5/1956 Burtner ........................ 544/330

FOREIGN PATENT DOCUMENTS 0124154 7/1984 European Pat. Off. .

Primary Examiner—Alan L. Rotman
Assistant Examiner—Robert C. Whittenbaugh
Attorney, Agent, or Firm—Ostrolenk, Faber, Gerb & Soffen

[57] ABSTRACT

There are described new pyrimidine derivatives of the general formula I

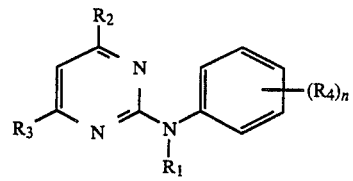

in which
n is 0, 1 or 2;
$R_1$ is
(a) the group —$CXR_5$, where X is oxygen or sulphur and $R_5$ is hydrogen, a nitrogen or sulphur containing heterocyclic group, which can contain other hetero atoms, optionally substituted alkenyl, acyl, alkoxycarbonyl, alkyl substituted by aryloxy, or optionally substituted mono- or dialkylamino; or $R_5$ is the group —$NHR_6$, where $R_6$ is substituted amino, substituted carbamoyl, optionally substituted alkylsulphonyl, acyl or arylsulphonyl, and when n is 0 or when X is sulphur, $R_5$ can also be alkyl, haloalkyl, aryl, aralkyl, alkoxycarbonylalkyl or arylamino;
(b) cyano or the group —$CXYR_7$, where X and Y are the same or different and are oxygen, sulphur or optionally substituted imino and $R_7$ is optionally substituted alkyl, aryl, acyl or a nitrogen or sulphur containing heterocyclic group, which can contain other hetero atoms; or
(c) when n is 1 or 2 and at least one $R_4$ group is haloalkoxy, $R_1$ can be hydrogen;
$R_2$ and $R_3$ are the same or different and are alkyl, and
$R_4$ is alkyl, alkoxy, halogen, haloalkyl, haloalkoxy, nitro or cyano. The compounds have fungicidal activity.

17 Claims, No Drawings

ANILINOPYRIMIDINE FUNGICIDES

Pyrimidine compounds with fungicidal activity are already known (e.g. DD PS No. 151,404 and 236,667).

According to the invention there are provided compounds of general formula I

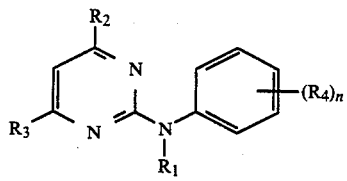

in which
n is 0, 1 or 2;
$R_1$ is (a) the group —$CXR_5$, where X is oxygen or sulphur and $R_5$ is hydrogen, a nitrogen or sulphur containing heterocyclic group, which can contain other hetero atoms, optionally substituted alkenyl, acyl, alkoxycarbonyl, alkyl substituted by aryloxy, or optionally substituted mono- or dialkylamino; or $R_5$ is the group —$NHR_6$, where $R_6$ is substituted amino, substituted carbamoyl, optionally substituted alkylsulphonyl, acyl or arylsulphonyl, and when n is 0 or when X is sulphur, $R_5$ can also be alkyl, haloalkyl, aryl, aralkyl, alkoxycarbonylalkyl or arylamino;

(b) cyano or the group —$CXYR_7$, where X and Y are the same or different and are oxygen, sulphur or optionally substituted imino and $R_7$ is optionally substituted alkyl, aryl, acyl or a nitrogen or sulphur containing heterocyclic group, which can contain other hetero atoms; or (c) when n is 1 or 2 and at least one $R_4$ group is haloalkoxy, $R_1$ can be hydrogen;

$R_2$ and $R_3$ are the same or different and are alkyl, and
$R_4$ is alkyl, alkoxy, halogen, haloalkyl, haloalkoxy, nitro or cyano.

Imino groups are preferably sustituted e.g. by alkyl or aryl. Alkyl and alkoxy groups are preferably of 1 to 7, e.g. 1 to 4 carbon atoms, especially methyl. Substituents, when present on any alkyl, alkylene or alkoxy group, include halogen, alkoxy (e.g. of 1 to 4 carbon atoms), hydroxy, alkylthio, nitro, optionally substituted amino, cyano, trialkylsilyl, carboxy, alkoxycarbonyl, acyloxy, aryl and heteroaryl. Alkenyl groups are generally of 2 to 4 carbon atoms and may be substituted e.g. by halogen or aryl. The term aryl means phenyl, optionally substituted, e.g. by halogen, alkyl, haloalkyl, alkoxy or nitro. The term heteroaryl includes groups such as furyl, pyridyl, imidazolyl, pyrazolyl, thienyl, pyridyl, triazolyl, tetrazolyl, benzimidazolyl and thiazolyl. By the term nitrogen or sulphur containing heterocyclic group is meant a nitrogen or sulphur containing groups such as those given under the term "heteroaryl", and non-aromatic groups such as morpholino, and piperidino. The term 'acyl' includes the residue of sulphonic and phosphorus containing acids as well as carboxylic acids. Acyl groups are preferably alkanoyl e.g. of 1 to 4 carbon atoms. Amino groups may be substituted, e.g. by one or two alkyl groups or two substituents can form a ring, e.g. to form a morpholino or piperidino ring.

It is generally preferred that $R_2$ and $R_3$ are both methyl. It is also preferred that n is 0. A particularly preferred group of compounds are those in which $R_1$ is —$COR_5$, where $R_5$ is 1-(1,2,4-triazolyl) or 1-imidazolyl or is —$COOR_7$, in which $R_7$ is $C_{1-7}$-alkyl, optionally substituted by $C_{1-7}$-alkylamino. Another valuable group of compounds are those where $R_1$ is —$CSR_5$, in which $R_5$ is hydrogen or alkyl.

The compounds of the invention have activity as fungicides, especially against fungal diseases of plants, e.g. Botrytis spp., especially *B. cinerea*; mildews and particularly barley powdery mildew (*Erysiphe graminis*), cucurbit powdery mildew (*E. cichoracearum*, and vine downy mildew (*Plasmopora viticola*), rice blast (*Pyricularia oryzae*) and wheat brown rust (*Puccinia recondita*). Other diseases against which the compounds may be active include apple scab (*Venturia inaequalis*), potato blight (*Phytophthora infestans*), bean rust (*Uromyces appendiculatus*), *Fusarium nivale* on rye, leaf spot, e.g. *Septoria nodorum* on wheat, and also bunt on wheat (*Tilletia caries*)

The invention thus also provides a method of combating a fungus at a locus infested or liable to be infested therewith, which comprises applying to the locus a fungicidally effective amount of a compound of the invention.

The invention also provides an agricultural composition comprising a compound of formula I in admixture with an agriculturally acceptable diluent or carrier.

The composition of the invention may of course include more than one compound of the invention. In addition the composition can comprise one or more additional active ingredients, for example compounds known to possess plant-growth regulant, herbicidal, fungicidal, insecticidal or acaricidal properties. If desired the compounds of the invention can be used in sequence with the other active ingredient.

The compounds of the invention show their activity both in pre- and post-emergent treatment.

The rates of use, depending on the target, amount in general to 0.005 to 5 kg of active agent/ha but can also be optionally higher. The time of application is determined by the target and the climatic conditions.

The compositions of the invention can take any form known in the art for the formulation of agrochemicals, for example, a solution, a dispersion, an aqueous emulsion, a dusting powder, a seed dressing, a fumigant, a smoke, a dispersible powder, an emulsifiable concentrate or granules. Moreover it can be in a suitable form for direct application or as a concentrate or primary composition which requires dilution with a suitable quantity of water or other diluent before application.

An emulsifiable concentrate comprises a compound of the invention dissolved in a water-immiscible solvent which is formed into an emulsion with water in the presence of an emulsifying agent.

A dusting powder comprises a compound of the invention intimately mixed and ground with a solid pulverulent diluent, for example, kaolin.

A granular solid comprises a compound of the invention associated with similar diluents to those which may be employed in dusting powders, but the mixture is granulated by known methods. Alternatively it comprises the active ingredient absorbed or adsorbed on a pre-granular diluent, for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the compound with water or other liquid, a wetting agent and a suspending agent.

The percentage of the active ingredient(s) in the various preparations can vary within wide limits. For example, the compositions can contain about 10 to 90 percent by weight active ingredients, and about 90 to 10 percent by weight liquid or solid carriers, as well as, optionally up to 20 percent by weight of surfactant.

The preparation of the formulations according to the invention can be carried out in a known manner, for example by milling or mixing processes. Optionally, individual components can be mixed just before use for example by the so-called tank-mixing method.

Formulations can be prepared, for example, from the following ingredients:

A. Wettable Powder (a)
40 percent by weight active ingredient
25 percent by weight bentonite
20 percent by weight silicic acid
10 percent by weight calcium lignosulphonate
5 percent by weight surface-active agent based on a mixture of calcium lignosulphonate and alkylphenol polyglycol ether (b)
25 percent by weight active ingredient
60 percent by weight kaolin
10 percent by weight silicic acid
5 percent by weight surface-active agent based on the sodium salt of N-methyl-N-oleyltaurine and calcium lignosulphonate (c)
10 percent by weight active ingredient
60 percent by weight bentonite
15 percent by weight silicic acid
10 percent by weight calcium lignosulphonate
5 percent by weight surface-active agent based on the sodium salt of N-methyl-N-oleyltaurine and calcium lignosulphonate B. Paste 45 percent by weight active ingredient
5 percent by weight sodium aluminium silicate
15 percent by weight cetylpolyglycol ether with 8 moles ethylene oxide
2 percent by weight spindle oil
10 percent by weight polyethylene glycol
23 parts water C. Emulsifiable concentrate 25 percent by weight active ingredient
15 percent by weight cyclohexanone
55 percent by weight xylene
5 percent by weight of mixture of nonylphenyl-polyoxyethylene or calcium dodecylbenzenesulphonate The compounds of the invention can be prepared in a variety of known ways. Thus in the case when $R_1$ is the group —$CXR_5$, where $R_5$ is (i) a heterocyclic group or an optionally substituted amino group or (ii) $NHR_6$, where $R_6$ is substituted amino or when $R_1$ is —$CXYR_7$, where X and Y are oxygen or sulphur, then a compound of formula II

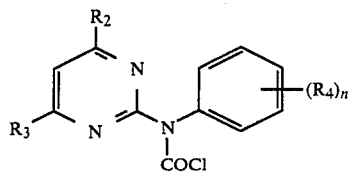

in which $R_2$, $R_3$ and $R_4$ have the meanings given above is reacted with a compound of formula $R_5H$ or $R_7YH$, in which $R_5$, $R_7$ and Y have the meanings given above.

Alternatively, a compound of the invention can be prepared by reacting a compound of formula I, where $R_1$ is hydrogen, with (i) a compound of formula $R_5CXCl$ or $R_7YCXCl$, (ii) with cyanogen bromide, when $R_1$ in formula I is cyano or (iii) with an isocyanate when $R_5$ is substituted amino or with a sulphonyl isocyanate when $R_6$ is alkyl- or arylsulphonyl. This reaction is generally carried out in the presence of an inert solvent such as diethyl ether, tetrahydrofuran, dimethylformamide or dimethyl sulphoxide. Where the molecule which is eliminated is acidic, the reaction can advantageously be carried out under basic conditions. Where the compound of formula $R_5H$ or $R_7YH$ can form a salt, (e.g. in the case when $R_5H$ is triazole or imidazole or $R_7YH$ is a phenol) then it may be desirable that it is reacted as a salt, e.g. the sodium salt, which is generally formed in situ. The reaction temperature is generally from $-15°$ to $100°$ C., preferably between $20°$ and $50°$ C.

The compound of formula II can be prepared by reacting a compound of formula I, where $R_5$ is hydrogen, preferably in the form of a salt such as the sulphate or hydrochloride, with a compound such as phosgene or trichloromethyl chloroformate. The reaction is generally carried out in an inert solvent, e.g. in an aromatic hydrocarbon, such as toluene, at a temperature of around $100°$ C.

When $R_1$ is formyl the compounds of the invention can be prepared by reacting a compound of formula I, where $R_1$ is hydrogen, with formic-acetic anhydride. Compounds where X is sulphur can be obtained by sulphurising the corresponding compound where X is oxygen, e.g. with phosphorus pentasulphide.

When $R_5$ is the group —$NHR_6$ the compounds of the invention can be obtained by reacting a compound of formula I, where $R_1$ is hydrogen, with the corresponding isocyanate or isothiocyanate of formula $R_6NCX$.

Where $R_1$ is —$CXYR_7$ and one of X and Y is an imino group, the compounds of the invention can be obtained by reacting the compound of formula I, where $R_1$ is hydrogen, with an isocyanate or isothiocyanate under basic conditions followed by reaction with a compound $R_7$Halogen.

Compounds of formula I where $R_1$ is hydrogen can be prepared by reacting a compound of formula IV

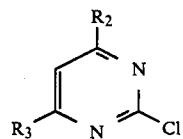

with a compound of formula V

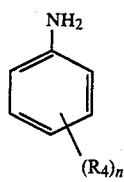

The compounds of formula IV and V are either known or can be prepared according to known methods.

The compounds of formula I where $R_5$ is hydrogen and $R_3$ and $R_4$ are different are novel and form part of the invention. The compounds of formula I, where $R_5$ is hydrogen and $R_3$ and $R_4$ are both ethyl are also novel and form part of the invention.

The invention is illustrated in the following Examples. Structures of isolated novel compounds were confirmed by elemental and/or other appropriate analyses. Temperatures are in °C.

EXAMPLE 1

2-Anilino-4,6-dimethylpyrimidine hydrochloride (100 g) was suspended in toluene (1200 ml). A slow stream of phosgene was passed through this over 5.5 hours at 108° (bath temperature of 120°) and then stirred for a further hour at the same temperature. After standing overnight, c. 300 ml of toluene was distilled at a bath temperature of 150°. It was then evaporated under reduced pressure. The oily residue was extracted twice with hexane (1000 ml) and the solution concentrated under reduced pressure. After a period of time crystals formed and these were separated to give N-(4,6-dimethylpyrimidin-2-yl)-N-phenylcarbamoyl chloride. This was shown by thin layer chromatography to be a uniform product, which was used without further purification.

Sodium triazole (54.6 g) was added portionwise to a solution of this product (78.53 g) in tetrahydrofuran (THF) (700 ml). The internal temperature rose to 32° over 12 minutes. It was then stirred overnight, filtered and the remaining solution concentrated in vacuo. After stirring with dry diisopropyl ether, there was obtained N-(4,6-dimethylpyrimidin-2-yl)-N-phenyl-1,2,4-triazole-1-carboxamide, as colourless crystals, m.p. 157°. (Compound 1).

EXAMPLE 2

Dry calcium carbonate (3.06 g) was added portionwise with vigorous stirring to a solution of N-(4,6-dimethylpyrimidin-2-yl)-N-phenylcarbamoyl chloride (4.0 g) in methanol (100 ml). The mixture was then heated to 50° and after 15 minutes worked up. The inorganic salt was filtered off and the mother liquor concentrated. After treatment with ether, the insoluble calcium chloride was filtered and the filtrate concentrated whereby methyl N-(4,6-dimethylpyrimidin-2-yl)-N-phenylcarbamate. m.p. 97°–100°, crystallised out. (Compound 2).

EXAMPLE 3

2-Anilino-4,6-dimethylpyrimidine (10 g) was added to formic-acetic anhydride (prepared from formic acid (5 ml) and acetic anydride (12 ml)) and the mixture heated gently to 40° to give a clear solution. After standing for 4 days, a crystalline solid separated and toluene was added to give a clear solution again. The mixture was evaporated to dryness, more toluene added and reevaporated. The product was recrystallised from ethyl acetate/light petroleum to give N-(4,6-dimethylpyrimidin-2-yl)-formanilide, m.p. 134°–5°. (Compound 3).

EXAMPLE 4

A mixture of the product from Example 3 (4.5 g) and phosphorus pentasulphide (5 g) in dry benzene (150 ml) was heated at reflux for 2½ hours. The mixture was filtered and the filtrate was treated whilst hot with charcoal and re-filtered. The filtrate was evaporated and the residue extracted with toluene. The extract was filtered and allowed to crystallise. The solid was recrystallised from toluene-light petroleum to give N-(4,6-dimethylpyrimidin-2-yl)thioformanilide, m.p. 161°–5°–163°. (Compound 4)

EXAMPLE 5

Methylsulphonyl isocyanate (3.15 g) was added dropwise to a solution of 2-anilino-4,6-dimethylpyrimidine (3.98 g) in toluene (40 ml). The mixture was then stirred for 2 hours at room temperature. The solid was separated and dried in vacuo, to give 1-(4,6-dimethylpyrimidine-2-yl)-3-methylsulphonyl-1-phenylurea, m.p. 186°–192°. (Compound 5).

EXAMPLE 6

Aqueous sodium hydroxide (130 ml of 40% solution) was added to a stirred solution of 4-nitrophenol (50 g) in dioxan (450 ml). The mixture was heated to 80° and, with stirring, chlorodifluoromethane was bubbled through over 20 hours at a rate such that no gas was exhausted. The mixture was then filtered, the filtrate evaporated and the residue extracted with ether. The extract was washed with aqueous sodium hydroxide, dried and evaporated to give 1-difluoromethoxy-4-nitrobenzene. This was then converted by treatment in a conventional manner with zinc and ammonium chloride to give 4-difluoromethoxyaniline as a yellow oil. 2-Chloro-4,6-dimethylpyrimidine (4.7 g) was added with stirring to this product (6 g) followed by concentrated hydrochloric acid (0.25 ml) and the mixture heated to 140°. It was then cooled, added to aqueous sodium hydroxide and extracted with ethyl acetate. The extract was washed with aqueous sodium chloride, dried and evaporated. The residue was recrystallised from diisopropyl ether in light petroleum to give 2-(4-difluoromethoxyanilino)-4,6-dimethylpyrimidine, m.p. 81°–2°. (Compound 6).

EXAMPLE 7

2-Anilino-4,6-dimethylpyrimidine (10 g) was added to a suspension of sodium hydride in oil (1.65 g of an 80% suspension) in dry THF (100 ml) and the mixture was heated under reflux until evolution of hydrogen ceased. Phenyl isothiocyanate (6.6 ml) was added slowly to the clear solution. The mixture was then stirred at room temperature for 2 hours. The solid was collected, washed with ether and dried in vacuo to give crude N-(4,6-dimethylpyrimidin-2-yl)-N,N'-diphenylisothiourea sodium salt. To a stirred solution of this product (7.2 g) in dimethyl sulphoxide (10 ml) was added a solution of methyl iodide (1.3 ml) in dimethyl sulphoxide (10 ml). The mixture was stirred at room temperature for 3 hours and then concentrated. The residue was treated with water and then extracted with dichloromethane. The extract was worked up in conventional manner to give N-(4,6-dimethylpyrimidin-2- yl)-S-methyl-N,N'-diphenylisothiourea, m.p. 101°–3°. (Compound 7).

EXAMPLE 8

A solution of 2-anilino-4,6-dimethylpyrimidine (5 g) in toluene was added to a suspension of sodium hydride in oil (0.75 g of an 80% suspension) in toluene (100 ml) and the mixture was heated under reflux until evolution of hydrogen ceased. A solution of trichloroacetyl chloride (2.8 ml) in toluene (20 ml) was added dropwise at room temperature and the mixture heated at 80° for one hour. It was then worked up by filtration through silica using dichloromethane as eluent. The solvent was evaporated and the residue, after solidification, was recrystallised from ethyl acetate/diisopropyl ether to give N-(4,6-dimethylpyrimidin-2-yl)-N-phenyltrichloroacetamide, m.p. 125.5°–7°. (Compound 8).

EXAMPLE 9

In a similar manner to that described in one of the previous Examples, the following compounds were obtained:

In the table the following abbreviation are used:
Tr = 1,2,4-triazol-1-yl;
Im = 1-imidazolyl;
Py = 1-pyrazolyl;
Te = 1-tetrazolyl;
Be = 1-benzimidazolyl;
Th = 2-thienyl;
Suc = succinimido;
Mo = morpholino;
Pip = piperidino;
Pyr(4) = 4-pyridyl;
Pyr(2) = 2-pyridyl;
Me = methyl;
Et = ethyl;
Pr = propyl;
Ph = phenyl;
Fu = 2-furyl.

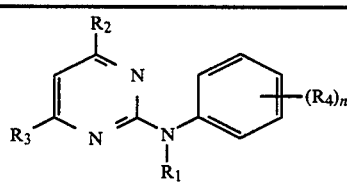

(I)

| Cpd no. | $R_2$ | $R_3$ | $R_1$ | $(R_4)_n$ | Physical constant m.p. (°) or $n_D^{RT}$ |
|---|---|---|---|---|---|
| 9 | Me | Me | COTr | 3-Cl— | 120–1 |
| 10 | Me | Me | COTr | 2-Cl— | 119–20 |
| 11 | Me | Me | COTr | 2,6-Me₂— | 171–2 |
| 12 | Me | Me | COTr | 2,4-Cl₂— | 121–2 |
| 13 | Me | Me | COIm | 4-Cl— | 169–70 |
| 14 | Me | Me | COIm | 3-Cl— | 123–4 |
| 15 | Me | Me | COIm | 2-Cl— | 131–2 |
| 16 | Me | Me | COOEt | — | 78–80 |
| 17 | Me | Me | COOC₇H₁₅ | — | 150 |
| 18 | Me | Me | COOC₈H₁₇ | — | 47–8 |
| 19 | Me | Me | COO(CH₂)₂NMe₂ | — | 1.5472 |
| 20 | Me | Me | COMe | — | 65–8 |
| 21 | Me | Me | COOC₁₅H₃₁ | — | 76–8 |
| 22 | Me | Me | COPh | — | 168–71 |
| 23 | Me | Me | COIm | — | 126–7 |
| 24 | Me | Me | COCF₃ | — | 139–41 |
| 25 | Me | Me | COCOOEt | — | 128–30 |
| 26 | Me | Me | COMe | 3,5-Cl₂— | 136–7 |
| 27 | Me | Me | COcyclopropyl | 3,5-Cl₂— | 128–30 |
| 28 | Me | Me | COCH₂OMe | 2,6-Me₂— | 86–7 |

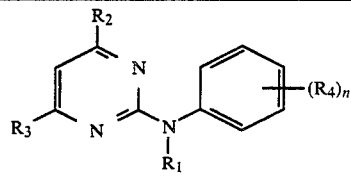

(I)

| Cpd no. | $R_2$ | $R_3$ | $R_1$ | $(R_4)_n$ | Physical constant m.p. (°) or $n_D^{RT}$ |
|---|---|---|---|---|---|
| 29 | Me | Me | COcyclopropyl | 2,6-Me₂— | 123–4 |
| 30 | Me | Me | COO—(2-MeOCO—Ph) | — | 140–2 |
| 31 | Me | Me | COO—(4-NO₂—Ph) | — | 134–6 |
| 32 | Me | Me | COO—Suc | — | 198–200 |
| 33 | Me | Me | CONHCH₂CN | — | 188–90 |
| 34 | Me | Me | COMo | — | 142–3 |
| 35 | Me | Me | CONHNMe₂ | — | 135–6 |
| 36 | Me | Me | CONHPip | — | 138–9 |
| 37 | Me | Me | CONHCONHPh | 3-MeO— | 164–5 |
| 38 | Me | Me | CONHSO₂(2-ClPh) | 2-Cl | 97–101 |
| 39 | Me | Me | CONHSO₂(2-ClPh) | 4-Cl | 183–5 |
| 40 | Me | Me | COTh | — | 101–3 |
| 41 | Me | Me | COPy | — | 142–3 |
| 42 | Me | Me | COTe | — | 143–5 |
| 43 | Me | Me | COBe | — | 163–4 |
| 44 | Et | Me | H | — | 1.616 |
| 45 | Et | Me | COTr | — | 97–8 |
| 46 | Et | Me | COIm | — | 113–4 |
| 47 | Pr | Me | H | — | 1.604 |
| 48 | Pr | Me | COTr | — | 107–8 |
| 49 | Me | Me | CSMe | — | 117.5–119 |
| 50 | Me | Me | CSPh | — | 117.5–9 |
| 51 | Me | Me | CSNHPh | — | 127–127.5 |
| 52 | Me | Me | CO—(4-NO₂—C₆H₄) | — | 247–9 |
| 53 | Me | Me | COOPh | — | 99–100 |
| 54 | Me | Me | COOPyr(4) | — | 182–4 |
| 55 | Me | Me | CONH—(4-NO₂—C₆H₄) | — | 201–3 |
| 56 | Me | Me | CONHCH₂COOH | — | 183–4 |
| 57 | Me | Me | CONHCONHPh | — | 165–8 |
| 58 | Me | Me | COTr | 4-OCF₂H | 132–3 |
| 59 | Me | Me | COTr | 4-Cl— | 141–2 |
| 60 | Me | Me | CONHSO₂(2-ClPh) | — | 175–7 |
| 61 | Me | Me | COCH₂O(4-ClPh) | — | 145–8 |
| 62 | Me | Me | CONHPr$^i$ | 3,5-Cl₂ | 136 |
| 63 | Me | Me | CONHCO(2-MePh) | — | 157–60 |
| 64 | Et | Et | H | — | 1.604 |
| 65 | Et | Et | COIm | — | 104–6 |
| 66 | Me | Me | CONHSO₂(2-COOEt—Ph) | — | 159–62 |
| 67 | Me | Me | CONHSO₂Ph | — | 180 |
| 68 | Me | Me | COO(CH₂)₂F | — | 1.551 |
| 69 | Me | Me | COO(CH₂)₂CN | — | 1.557 |
| 70 | Me | Me | COO(CH₂)₂SiMe₃ | — | 1.534 |
| 71 | Me | Me | COCH₂COOEt | — | 87–88.5 |
| 72 | Me | Me | COCH=CH₂ | — | 76–9 |
| 73 | Me | Me | COCH=CHPh | — | 108 |
| 74 | Me | Me | COOCH₂Fu | — | 107–8 |
| 75 | Et | Et | COTr | — | 71–2 |
| 76 | Pr | Me | COIm | — | 109–110 |
| 77 | Me | Me | CONH₂ | — | >275 |
| 78 | Me | Me | SO₂(4-MePh) | — | 189–90 |
| 79 | Me | Me | CSNMe₂ | — | 133–4 |
| 80 | Et | Et | CHO | — | 84–6 |
| 81 | Me | Pr | CHO | — | 88–9 |
| 82 | Et | Et | CHS | — | 59–60 |
| 83 | Me | Pr | CHS | — | 50–2 |
| 84 | Me | Me | COEt | — | 77.5–79 |
| 85 | Me | Me | COO(CH₂)₃Cl | — | 1.562 |
| 86 | Me | Me | COOCH(Me)COOEt | — | 62–3 |
| 87 | Me | Me | CSEt | — | 96–8 |
| 88 | Me | Me | COSPh | — | 136–136.5 |
| 89 | Me | Me | COSPyr(2) | — | 137–137.5 |
| 90 | Me | Me | COO(CH₂)₂OMe | — | 1.552 |
| 91 | Me | Me | CHS | 4-CHF₂— | |
| 92 | Me | Me | COCOMe | — | |
| 93 | Me | Me | COCH₂OPh | — | |

EXAMPLE 10

2-Anilino-4,6-dimethylpyrimidine (3.98 g) was treated with sodium hydride in a similar manner to that described in Example 8. The resulting sodium salt was then treated with cyanogen bromide (2.12 g) and the mixture heated under reflux for 4 hours. The mixture was then filtered through silica gel and eluted with dichloromethane and the solution evaporated. The residue was recrystallised from ethyl acetate to give N-(4,6-dimethylpyrimidin-2-yl)-N-phenylcyanamide, m.p. 153°-4°. (Compound 94).

TEST EXAMPLE

The compounds of the invention were subjected to various tests.

(a) Foliar tests

Compounds were assessed for activity against one or more of the following:

*Erysiphe graminis:* barley powdery mildew (EG)
*Erysiphe cichoracearum:* cucurbit powdery mildew (EC)
*Plasmopara viticola:* vine downy mildew (PV)
*Pyricularia oryzae:* rice blast (PO)
*Botrytis cinerea:* grey mould of tomato (BC)

Aqueous solutions or dispersions of the compounds at the desired concentration, including a wetting agent, were sprayed onto the appropriate plant and then inoculated by spraying with spore suspensions of the fungi or by dusting or shaking diseased material over the treated plants for the Erysiphe spp.. Plants were then kept under controlled environment conditions suitable for maintaining plant growth and development of the disease. After an appropriate time, the degree of infection of the leaf surface is visually estimated.

Compounds were considered active if they gave greater than 50% control of the disease at a concentration of 500 ppm (w/v) or less.

(b) Soil pathogen test

In these tests compounds were assessed for activity against *Rhizoctonia solani* (RS)

Flasks containing maize meal/sand were inoculated with the test fungus and then incubated. The maize meal/sand cultures were used to infest potting compost which was then put into plastic pots. Aqueous solutions or dispersions of the compounds, including a wetting agent, were added to the pots to give a desired concentration of compound in each pot. Control pots were set up by adding similar solutions or dispersions without the test compound Immediately after application of the test compound each pot was sown with a number of cabbage seeds. The seeds were covered with treated infested soil and the pots incubated under controlled environment conditions suitable for plant growth and development of the disease. The number of emerged cabbage seedlings is counted and percentage disease control calculated by comparison with the untreated infested pots.

Compounds were considered active if they gave greater than 50% control of the disease at a concentration of 300 parts by weight of compound or less per million parts by volume of soil.

Activities were demonstrated as follows (+ =active).

| Compound No | BC | EG | EC | PV | PO | RS |
|---|---|---|---|---|---|---|
| 1 | + | + | | | | |
| 2 | + | + | | | | |
| 3 | | | + | | | |
| 4 | + | | | + | | |
| 5 | + | + | | | | |
| 6 | + | + | | | | + |
| 9 | | + | + | + | | + |
| 10 | | | + | + | | + |
| 11 | | | + | | | + |
| 12 | | | + | | | + |
| 13 | | + | + | + | + | + |
| 14 | | + | + | + | + | |
| 15 | | + | | | | + |
| 16 | | | + | | | |
| 17 | | + | + | | | |
| 18 | | + | + | | | |
| 19 | | + | + | | | |
| 20 | | + | | | | |
| 21 | | | + | | | |
| 22 | | | + | | | |
| 23 | | + | + | + | + | |
| 24 | | | | | | |
| 25 | | | | | | |
| 26 | | | + | | | |
| 27 | | | + | | | |
| 28 | | | + | | | |
| 29 | | | + | | | |
| 37 | | | + | | | |
| 38 | | + | | | | |
| 39 | | + | | | | |
| 45 | + | | | | | |
| 46 | + | + | | | | |
| 59 | | | + | + | + | + |
| 60 | + | + | | | | |
| 61 | | | + | + | | |
| 62 | | | + | | | |
| 63 | | + | + | | | |
| 66 | + | + | | | | |
| 67 | + | | | | | |

We claim:
1. A compound of formula I

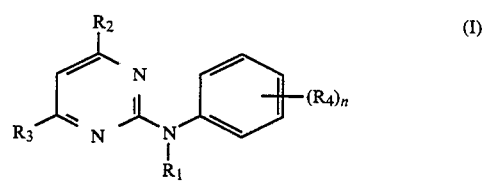

in which
n is 0, 1 or 2;
$R_1$ is
(a) the group —$CXR_5$, where X is oxygen or sulphur and $R_5$ is hydrogen, a nitrogen or sulphur containing heterocyclic selected from the group consisting of pyridyl, imidazolyl, pyrazolyl, thienyl, pyridyl, triazolyl, tetrazolyl, benzimidazolyl, thiazolyl, morpholino, piperidino, and succinimido; $C_{2-4}$-alkenyl, (optionally substituted by phenyl), $C_{1-4}$-alkanoyl, $C_{1-7}$-alkoxycarbonyl, $C_{1-7}$-alkyl substituted by phenoxy (optionally substituted by halogen), or amino substituted by mono- or di-$C_{1-7}$-alkyl; or $R_5$ is the group —$NHR_6$, where $R_6$ is amino substituted by mono- or di-$C_{1-7}$-alkyl, carbamoyl substituted by phenyl (optionally halo substituted), $C_{1-7}$-alkyl-sulphonyl or phenylsulphonyl (optionally halo substituted), and when n is 0 or when X is sulphur, $R_5$ can also be $C_{1-7}$ alkyl, halo-$C_{1-7}$-alkyl, phenyl, aralkyl, $C_{1-7}$-alkoxycarbonyl-$C_{1-7}$-alkyl or phenylamino;

(b) cyano or the group —$CXYR_7$, where X and Y are the same or different and are oxygen, sulphur and $R_7$ is $C_{1-7}$-alkyl (optionally subsituted by halogen, $C_{1-4}$-alkoxy, $C_{1-7}$-alkylamino, cyano, tri-$C_{1-7}$-alkylsilyl, phenyl, furyl, pyridyl, imidazolyl, pyrazolyl, thienyl, pyridyl, triazolyl, tetrazolyl, benzimidazolyl, thiazolyl, morpholino, piperidino or succinimido), phenyl, furyl, pyridyl, imidazolyl, pyrazolyl, thienyl, pyridyl, triazolyl, tetrazolyl, benzimidazolyl, thiazolyl, morpholino, piperidino or succinimido; or (c) when n is 1 or 2 and at least one $R_4$ group is halo-$C_{1-7}$-alkoxy, $R_1$ can be hydrogen;

$R_2$ and $R_3$ are the same or different and are $C_{1-7}$-alkyl, and $R_4$ is $C_{1-7}$-alkyl, $C_{1-7}$-alkoxy, halogen, halo-$C_{1-7}$-alkyl, halo-$C_{1-7}$-alkoxy, nitro or cyano.

2. A compound according to claim 1, in which $R_2$ and $R_3$ are both methyl.

3. A compound according to claim 1, in which n is 0.

4. A compound according to claim 1, in which $R_1$ is —$COR_5$, where $R_5$ is 1-(1,2,4-triazolyl) or 1-imidazolyl or is —$COOR_7$, in which $R_7$ is $C_{1-7}$-alkyl, optionally substituted by $C_{1-7}$-alkylamino.

5. A compound according to claim 1, in which $R_1$ is —$CSR_5$, wherein $R_5$ is hydrogen or $C_{1-7}$ alkyl.

6. A compound of formula I as in claim 1, in which $R_5$ is hydrogen, and $R_3$ and $R_4$ are different or are both ethyl.

7. A compound according to claim 1 in which each of said 1 to 7 carbon atom ranges is a range of 1 to 4 carbon atoms.

8. A compound according to claim 7 in which $R_2$ is methyl or ethyl, $R_3$ is methyl or ethyl, n is 0 and $R_1$ is $COR_5$ or $COOR_7$.

9. A compound according to claim 1, in which $R_2$ is methyl, ethyl or propyl, $R_3$ is methyl, ethyl or propyl, $(R_4)_n$ is absent or is chloro, dichloro, dimethyl, methoxy, difluoromethoxy or difluoromethyl, X is oxygen and Y is oxygen.

10. A fungicidal composition comprising a fungicidally effective amount of a compound as claimed in claim 1 in admixture with an agriculturally acceptable diluent or carrier.

11. A method of combating a fungus at a locus infested or liable to be infested therewith, which comprises applying to the locus a fungicidally effective amount of a compound as claimed in claim 1.

12. A method of combatting a fungus at a locus infested or liable to be infested therewith, which comprises applying to the locus a fungicidally effective amount of a compound as claimed in claim 7.

13. A method of combatting a fungus at a locus infested or liable to be infested therewith, which comprises applying to the locus a fungicidally effective amount of a compound as claimed in claim 8.

14. A method of combatting a fungus at a locus infested or liable to be infested therewith, which comprises applying to the locus a fungicidally effective amount of a compound as claimed in claim 9.

15. A fungicidal composition comprising a fungicidally effective amount of a compound as claimed in claim 7 in admixture with an agriculturally acceptable diluent or carrier.

16. A fungicidal composition comprising a fungicidally effective amount of a compound as claimed in claim 8 in admixture with an agriculturally acceptable diluent or carrier.

17. A fungicidal composition comprising a fungicidally effective amount of a compound as claimed in claim 9 in admixture with an agriculturally acceptable diluent or carrier.

* * * * *